United States Patent
Huang

(10) Patent No.: US 11,141,170 B2
(45) Date of Patent: *Oct. 12, 2021

(54) BONE DRILLING COVER DEVICE

(71) Applicant: OSSAWARE BIOTECH CO., LTD., Changhua County (TW)

(72) Inventor: Max Huang, Changhua County (TW)

(73) Assignee: OSSAWARE BIOTECH CO., LTD., Changhua County (TW)

( * ) Notice: Subject to any disclaimer, the term of this patent is extended or adjusted under 35 U.S.C. 154(b) by 154 days.

This patent is subject to a terminal disclaimer.

(21) Appl. No.: 16/558,156

(22) Filed: Sep. 2, 2019

(65) Prior Publication Data

US 2020/0085449 A1 Mar. 19, 2020

(30) Foreign Application Priority Data

Sep. 18, 2018 (TW) .................................. 107132861

(51) Int. Cl.
*A61B 17/16* (2006.01)
*A61B 17/00* (2006.01)

(52) U.S. Cl.
CPC ...... *A61B 17/1695* (2013.01); *A61B 17/1633* (2013.01); *A61B 2017/00477* (2013.01)

(58) Field of Classification Search
CPC ..... A61B 17/68; A61B 17/88; A61B 17/1633; A61B 17/1695; A61B 17/688; A61B 2017/00477; A61B 17/8875
See application file for complete search history.

(56) References Cited

U.S. PATENT DOCUMENTS

2008/0172097 A1* 7/2008 Lerch .................... A61B 17/688
606/324
2013/0282011 A1* 10/2013 Brogan .............. A61B 17/8872
606/75

FOREIGN PATENT DOCUMENTS

EP 3381388 A2 * 10/2018 ......... A61B 17/8875

* cited by examiner

*Primary Examiner* — George J Ulsh
(74) *Attorney, Agent, or Firm* — Leong C. Lei

(57) ABSTRACT

A bone drilling cover device comprises an upper fastening member and a lower fastening member. The upper fastening member includes a first base portion and a first coupling portion. The lower fastening member includes a second base portion and a second coupling portion engagable with the first coupling portion. The second base portion is composed of at least one first arm and at least one second arm. The first arm has a length greater than a length of the second arm. A total length of the first arm and the second arm is greater than a diameter of a drilled hole. Through the first arm and the second arm having different lengths, the first arm and the second arm can be inserted in an oblique manner and positioned to the underside of the drilled hole for covering the drilled hole of any bone.

15 Claims, 15 Drawing Sheets

BONE DRILLING COVER DEVICE

FIELD OF THE INVENTION

The present invention relates to a bone drilling cover device that can be widely used and improve work efficiency.

BACKGROUND OF THE INVENTION

Taiwan Patent Publication No. 1609670 discloses a cranial bone fixing device and a surgical tool thereof, owned by the applicant. The cranial bone fixing device comprises a lower fastening member and a movable retaining assembly. When the entire movable retaining assembly is positioned by the outer sleeve of the surgical tool, it can be arranged at a certain distance from the outer surface of the cranium to facilitate implantation and restoration of the cranial bone.

The aforementioned fixing device can provide a convenient and progressive clinical operation for fixing the cranial bone. However, the lower fastening member is a circular structure, and its outer diameter is greater than the inner diameter of the drilled hole, so it can only be used for fixing the original cut cranial bone to the cranium. As to a single drilled hole for the placement of a monitor, probe or drainage tube, because the lower fastening member cannot be inserted into the cranium via the drilled hole, the fixing device cannot be used for covering the drilled hole, and it is necessary to use another object for covering the drilled hole. As a result, the above invention cannot achieve the purpose of fixing the cranial bone and covering the drilled hole. In addition, if bone grafting is performed, it is necessary to drill a hole in part of the body such as the femur, the hand bone, the foot bone or the sternum; or when the surgical instrument needs to pass through the adjacent bone for surgical operation, it is also necessary to drill a hole in the bone. Similarly, the lower fastening member of the above-mentioned invention cannot be inserted into a single drilled hole, so it is not suitable for covering the single drilled hole. If the drilled hole is not covered to be in a hollow state, the soft and hard tissues are easily filled to affect the normal bone hyperplasia. Besides, if the drilled hole is not covered, it is easily damaged when touched by an external force. This is a problem that the medical staff is trying to solve.

Accordingly, the inventor of the present invention has devoted himself based on his many years of practical experiences to solve these problems.

SUMMARY OF THE INVENTION

The primary object of the present invention is to provide a bone drilling cover device, comprising an upper fastening member and a lower fastening member. The upper fastening member includes a first base portion and a first coupling portion disposed on the first base portion. The lower fastening member includes a second base portion and a second coupling portion that is disposed on the second base portion and engagable with the first coupling portion. The second base portion is composed of at least one first arm and at least one second arm. The first arm has a length greater than a length of the second arm. A total length of the first arm and the second arm is greater than a diameter of a drilled hole.

Preferably, the length of the second arm is greater than a radius of the drilled hole.

Preferably, the first arm and the second arm are in a platy shape having a width less than the diameter of the drilled hole with a center line of the second coupling portion as a center. The first arm is integrally formed with the second arm.

Alternatively, the first arm and the second arm are in a platy shape having a width less than the diameter of the drilled hole with a center line of the second coupling portion as a center. The first arm and the second arm are separate elements that are extendable and retractable and pivotally connected to each other.

Through the first arm and the second arm having different lengths, the lower fastening member is inserted in an oblique manner toward the drilled hole, such that the first arm and the second arm can be smoothly and quickly inserted and positioned to the underside of the drilled hole for covering the drilled hole of any bone. The operation is very quick and easy. The diameter of the drilled hole is minimized for reducing damage to the bone structure. When the invention is used for retaining the cranial bone, the first arm and the second arm are configured to span and hold the cranial bone and the cranium. The invention can be widely used to improve the shortcomings of the prior art.

Embodiments of the present invention will now be described, by way of example only, with reference to the accompanying drawings.

DETAILED DESCRIPTION OF THE PREFERRED EMBODIMENTS

Figure 1:
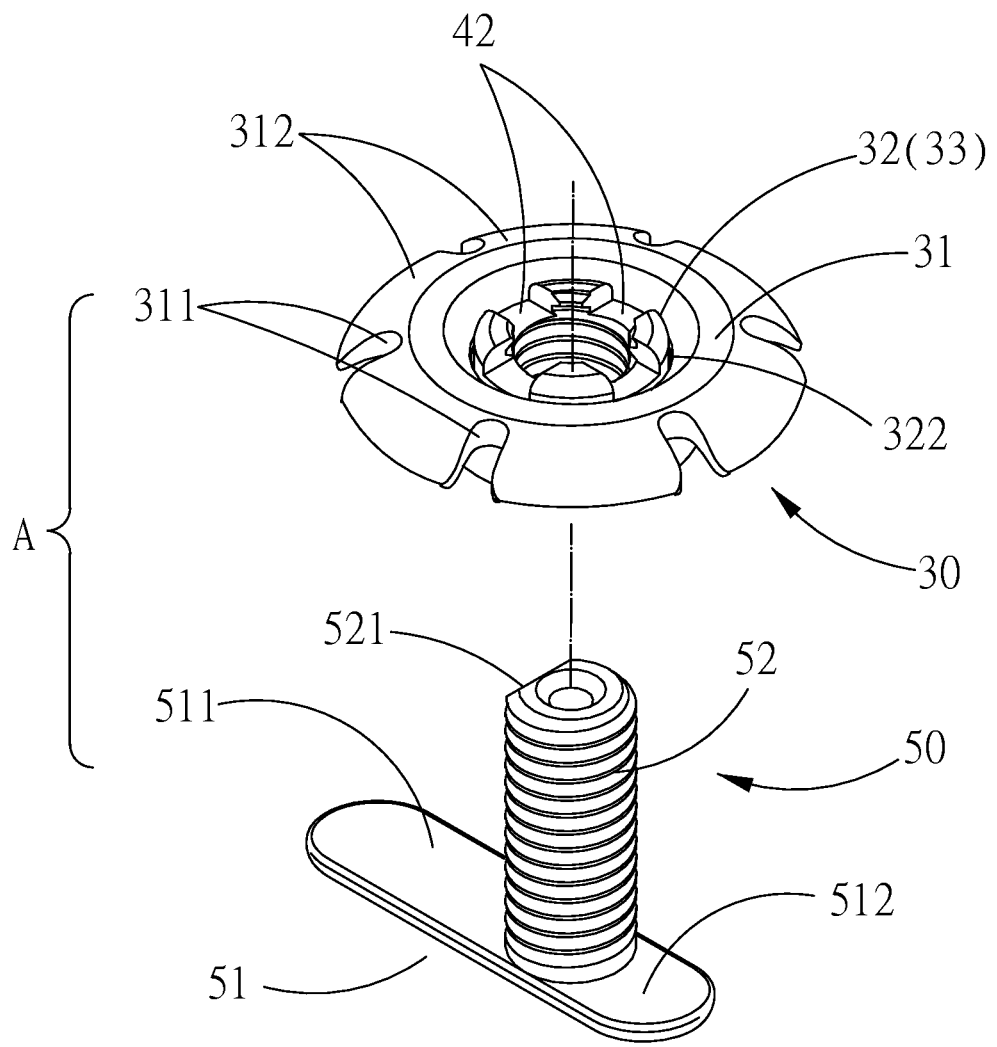
FIG. 1 is a top exploded view of the present invention.
Figure 2:
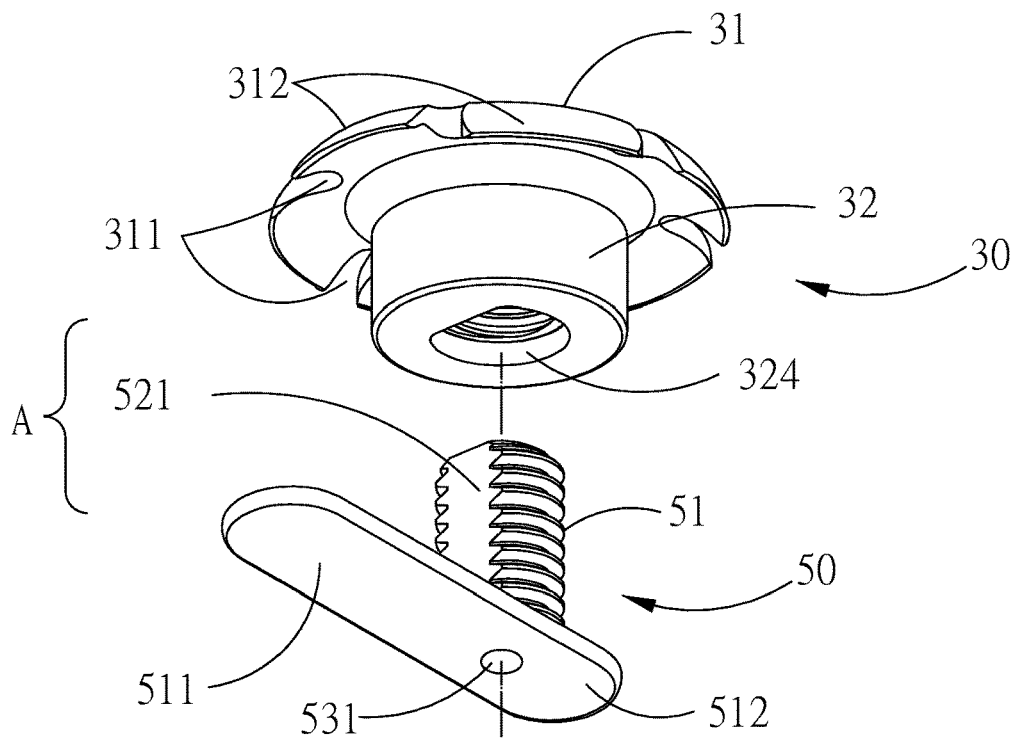
FIG. 2 is a bottom exploded view of the present invention.

First, as shown in FIGS. 1 to 16, the bone drilling cover device A of the present invention, regardless of covering a drilled hole of any bone, the connecting structure and operation of the bone drilling cover device A and the surgical tool B are similar to the technique as disclosed in Taiwan Patent Publication No. 1609670 filed by the same applicant, and will not be described hereinafter.

The following is an embodiment of the present invention used for covering a single drilled hole of the cranium. The present invention is applied to cover a drilled hole of any bone, and is not limited thereto.

As shown in FIGS. 1 to 7, the bone drilling cover device A of the present invention comprises an upper fastening member 30 and a lower fastening member 50.

The upper fastening member 30 includes a first base portion 31 and a first coupling portion 32 disposed on the first base portion 31. The first base portion 31 is in the form of a plate or a disk having an outer circumference that is formed with a plurality of spaced slits 311 to form a plurality of petal-like segments 312. The plurality of petal-like segments 312 each have a thickness that is gradually reduced toward its outer periphery so as to be secured to the cranium 70 easily. The first coupling portion 32 is an annular sleeve with a cavity portion 322 having a bottom in which a through hole 323 is formed. A nut 33 is disposed in the cavity portion 322. The inner surface of the cavity portion 322 is recessed to form an engaging groove 321. The through hole 323 is formed with an inner cut surface 324. A first positioning portion 42 is disposed on the periphery of the upper end of the nut 33 for connecting the surgical tool B. Preferably, the first positioning portion 42 is a concave-convex configuration annularly formed on the periphery of the upper end of the nut 33 or includes at least two pits (not shown) on the lower end surface of the nut 33. The outer surface of the nut 33 is provided with a raised ring 41 engagable with the engaging groove 321 on the inner surface of the cavity portion 322. When the nut 33 is screwed to a second coupling portion 52 (screw rod) of the lower fastening member 50, the upper fastening member 30 is not rotated synchronously, but can be moved up and down by the nut 33. The nut 33 and the upper fastening member 30 collectively form a movable retaining assembly.

The lower fastening member 50 includes a platy second base portion 51 having a proper width and a second coupling portion 52. The second coupling portion 52 is a screw rod to be screwed to the nut 33. The second coupling portion 52 (screw rod) is formed with an inner screw hole 53 for connecting the surgical tool B. The second coupling portion 52 (screw rod) is formed with an outer cut surface 521 corresponding to the inner cut surface 324 of the through hole 323. The second base portion 51 is composed of a first arm 511 and at least one second arm 512. The first arm 511 and the second arm 512 have different lengths with a center line Z of the second coupling portion 52 (screw rod) as a center. The total length X+Y of the first arm 511 and the second arm 512 is greater than the diameter D of a drilled hole 73. The length X of the first arm 511 is greater than the length Y of the second arm 512. The length Y of the second arm 512 is greater than the radius R1 of the drilled hole 73; alternatively, the length Y of the second arm 512 is greater than the radius R2 of the first coupling portion 32 (annular sleeve). Although the length Y of the second arm 512 is greater than the radius R1 of the drilled hole 73, for the surgical operation, it is only required to move the device toward the second arm 512 after insertion for the first coupling portion 32 (annular sleeve) to be against the inner wall of the drilled hole 73, such that the first arm 511 and the second arm 512 are respectively positioned across the underside of the drilled hole 73. The width of the second base portion 51 is less than the diameter of the drilled hole 73.

Figure 5:
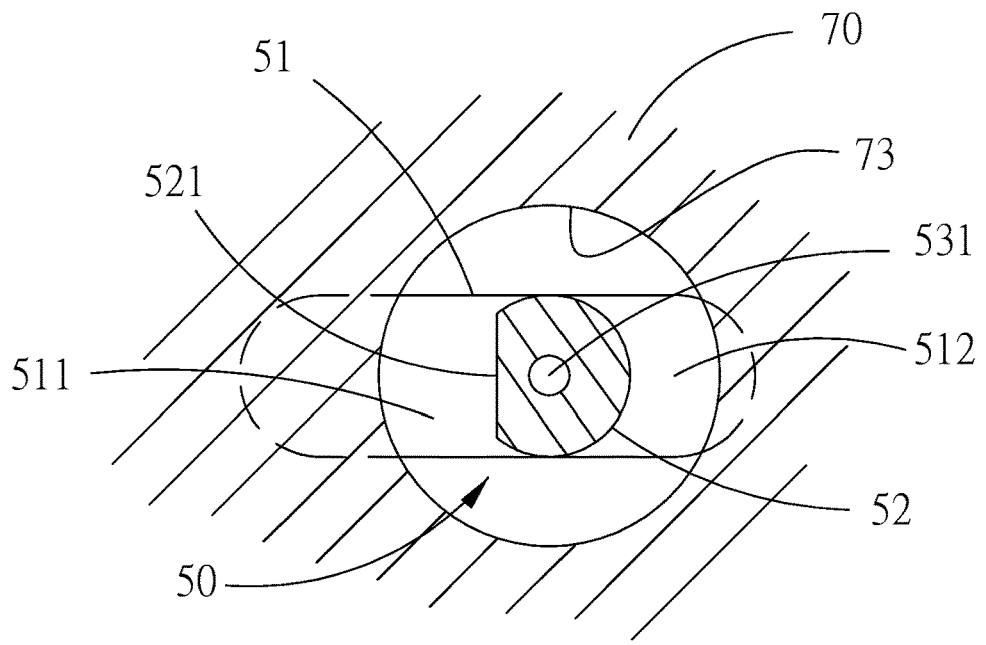
FIG. 5 is a sectional view taken along line A-A of FIG. 4.
Figure 6:
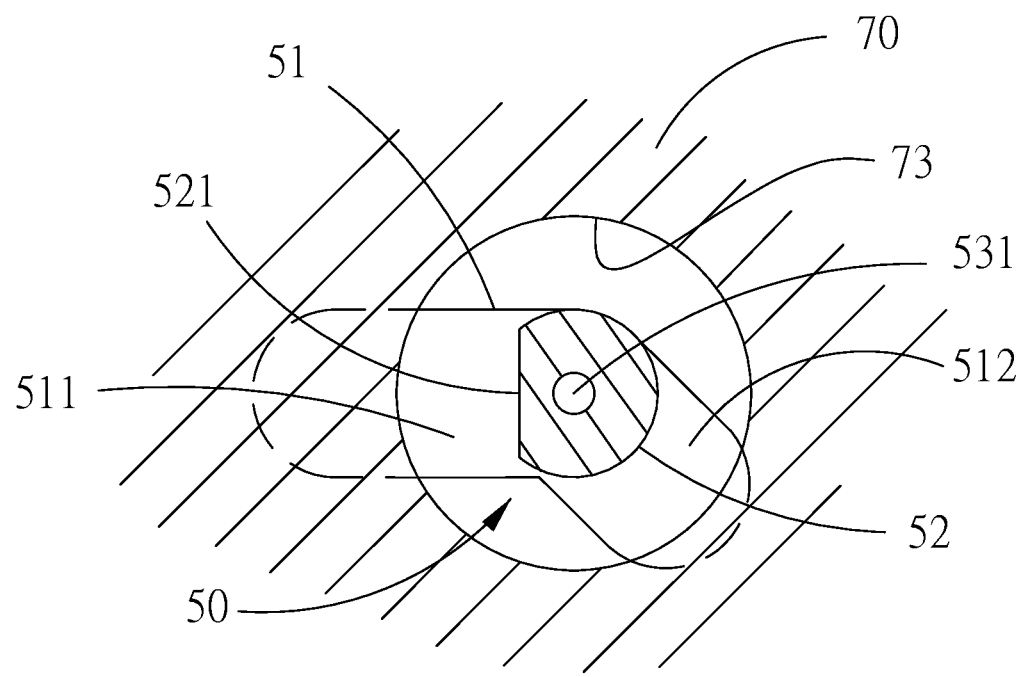
FIG. 6 is a schematic view showing the first arm and the second arm that are connected and arranged at an angle according to the present invention.
Figure 7:
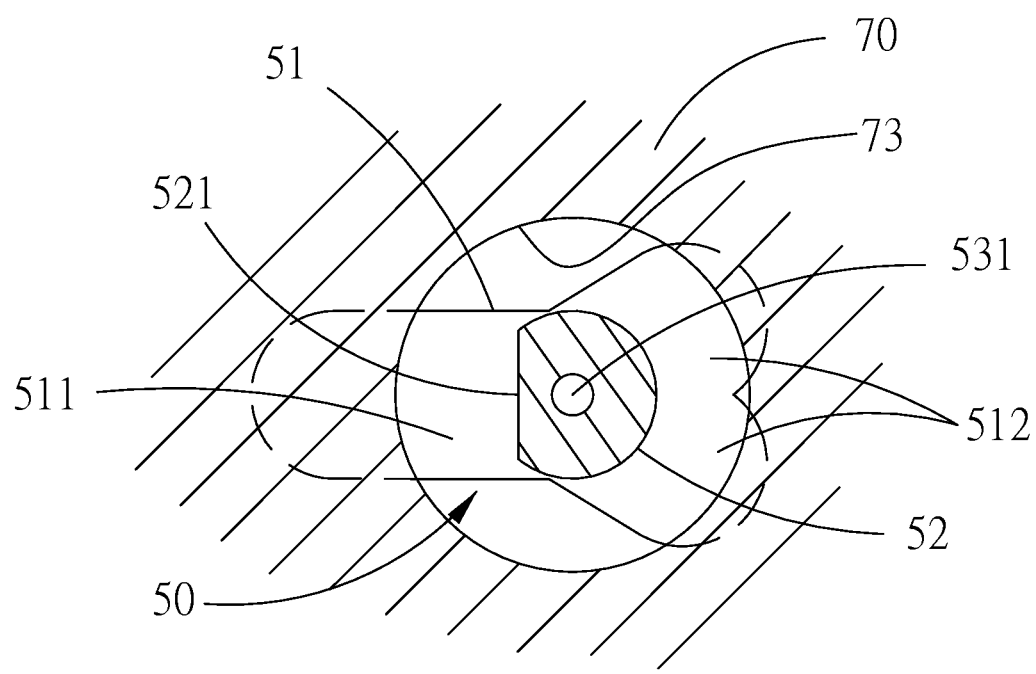
FIG. 7 is a schematic view showing the first arm and the second arm that are connected and arranged in a Y shape according to the present invention.
Figure 8:
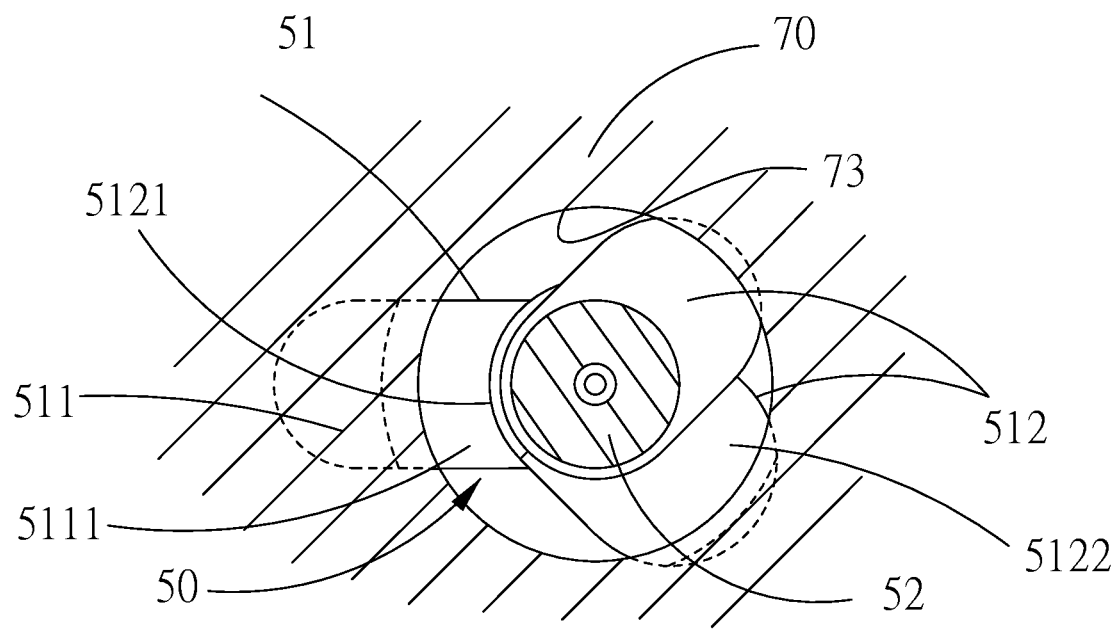
FIG. 8 is a schematic view showing the first arm and the second arm in an extended state according to the present invention.
Figure 9:
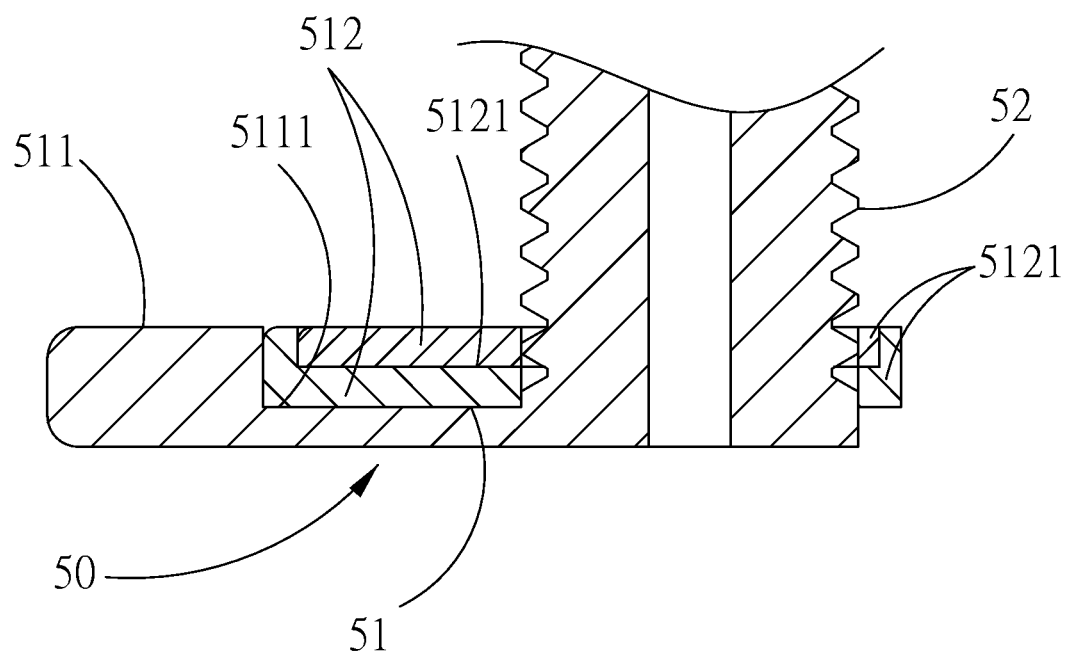
FIG. 9 is a sectional schematic view showing the first arm and the second in a retracted state according to the present invention.
Figure 10:
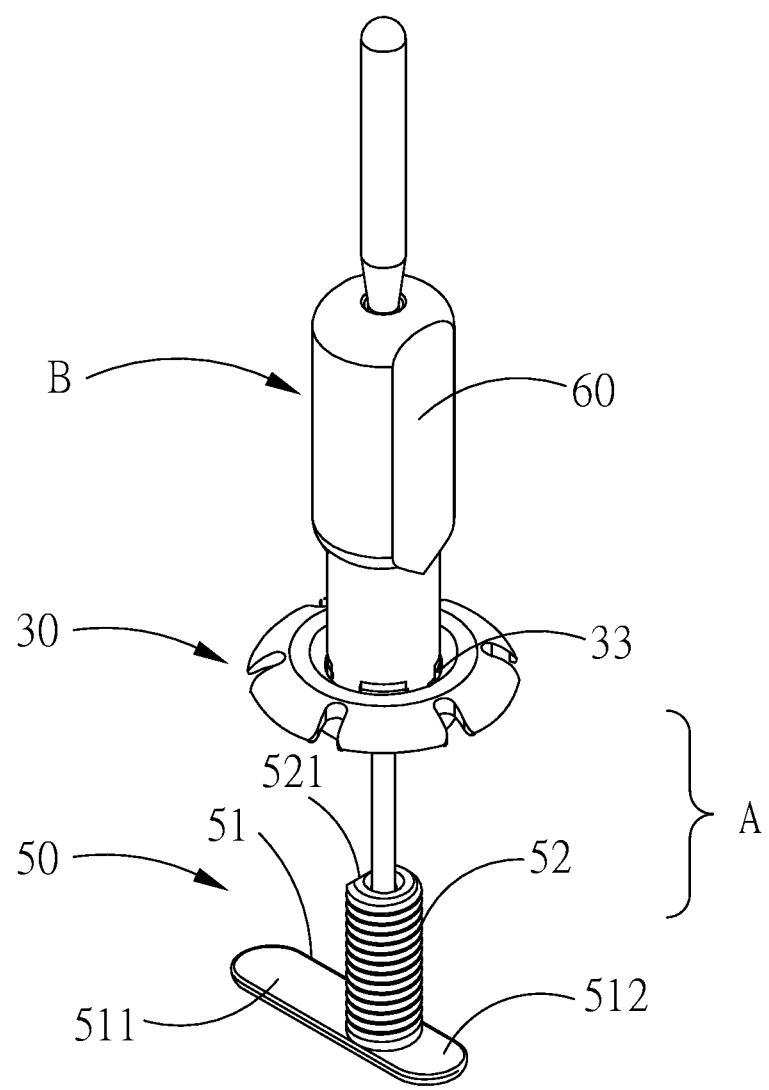
FIG. 10 is a perspective view of the present invention combined with the surgical tool.
Figure 11:
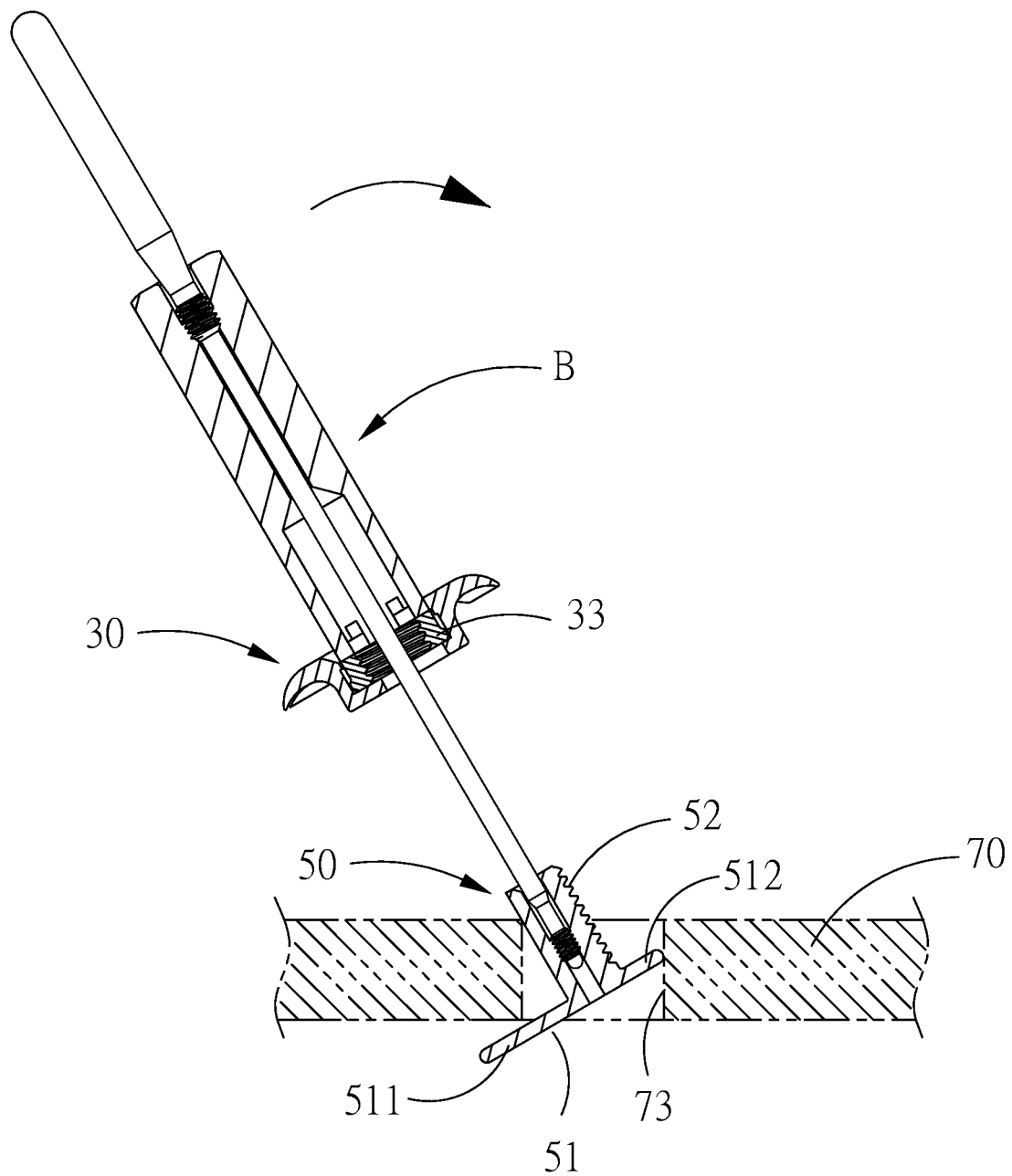
FIG. 11 is a schematic view showing the operation that the lower fastening member is inserted in an oblique manner toward the drilled hole according to the present invention.
Figure 12:
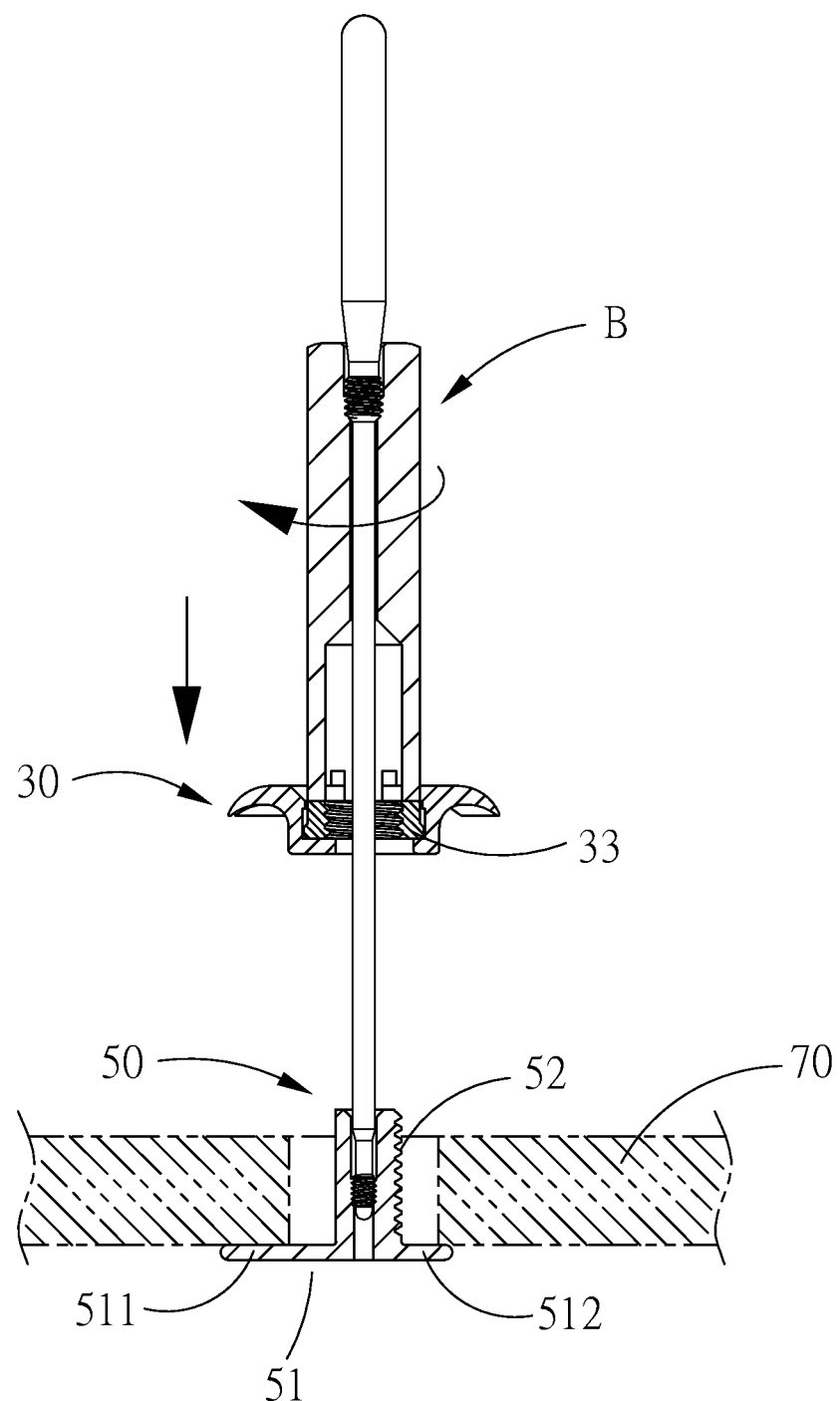
FIG. 12 is a schematic view showing the operation that the first arm and the second arm are positioned to the underside of the drilled hole according to the present invention.
Figure 13:
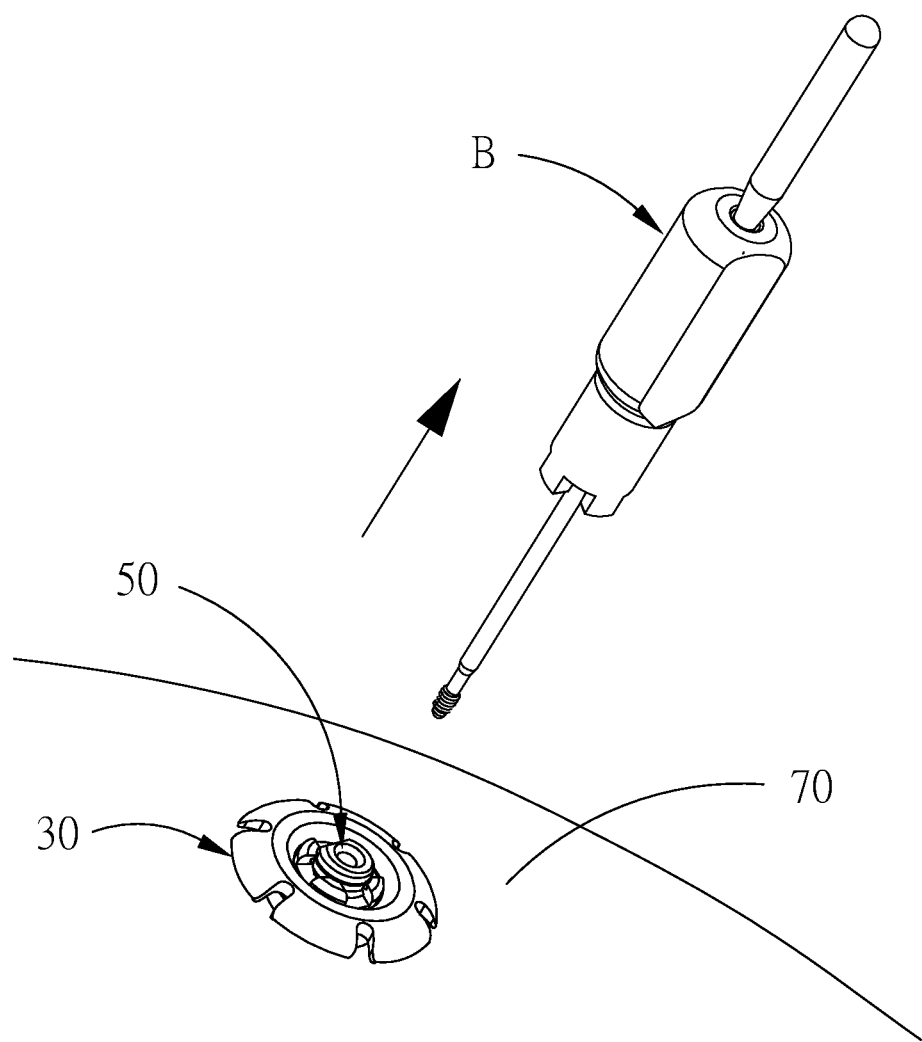
FIG. 13 is a schematic view showing that the surgical tool is pulled out after the upper fastening member and the lower fastening member are fastened to cover the drilled hole according to the present invention.

As shown in FIGS. 5 to 7, the first arm 511 and the second arm 512 are connected and arranged in a line or at an angle or in a Y shape with the center line Z of the second coupling portion 52 (screw rod) as the center, and the first arm 511 is integrally formed with the second arm 512; or as shown in FIG. 8 and FIG. 9, the first arm 511 and the second arm 512 are separate elements, that is, the first arm 511 is formed by extending the second coupling portion 52 (screw rod), and the first arm 511 is formed with a recess 5111 for the second arm 512 to be received into the recess 5111, and the second arm 512 has a sleeve portion 5121 fitted onto the second coupling portion 52 (screw rod), so that the second arm 512 is pivotable about the second coupling portion 52 (screw rod). As shown in the figures, the second arm 512 is plural, and the second arms 512 are respectively pivoted to the second coupling portion 52 (screw rod). The lower second arm 512 is received into the recess 5122 for the upper second arm 512 to be overlapped and movably pivoted.

FIGS. 4 to 13 illustrate the operation of the present invention used for bone drilling. The bone drilling cover device A of the present invention is first coupled with the surgical tool B to form an integral assembly. The invention is characterized in that the second base portion 51 of the lower fastening member 50 is in a platy shape having a proper width and that the first arm 511 and the second arm 512 have different lengths. Therefore, the whole assembly is taken in an oblique manner and the lower fastening member 50 is inserted in an oblique manner toward the drilled hole 73, such that the first arm 511 and the second arm 512 can be smoothly and quickly positioned in the drilled hole 73 across the underside of the drilled hole 73. When the upper fastening member 30 is moved downwardly by the surgical tool B to screw the nut 33 downwardly to the second coupling portion 52 (screw rod) of the lower fastening member 50, the nut 33 synchronously drives the upper fastening member 30 to be moved downwardly and tightly positioned with the first arm 511 and the second arm 512, and the upper fastening member 30 covers the drilled hole 73. It is convenient and quick for operation.

Figure 14:
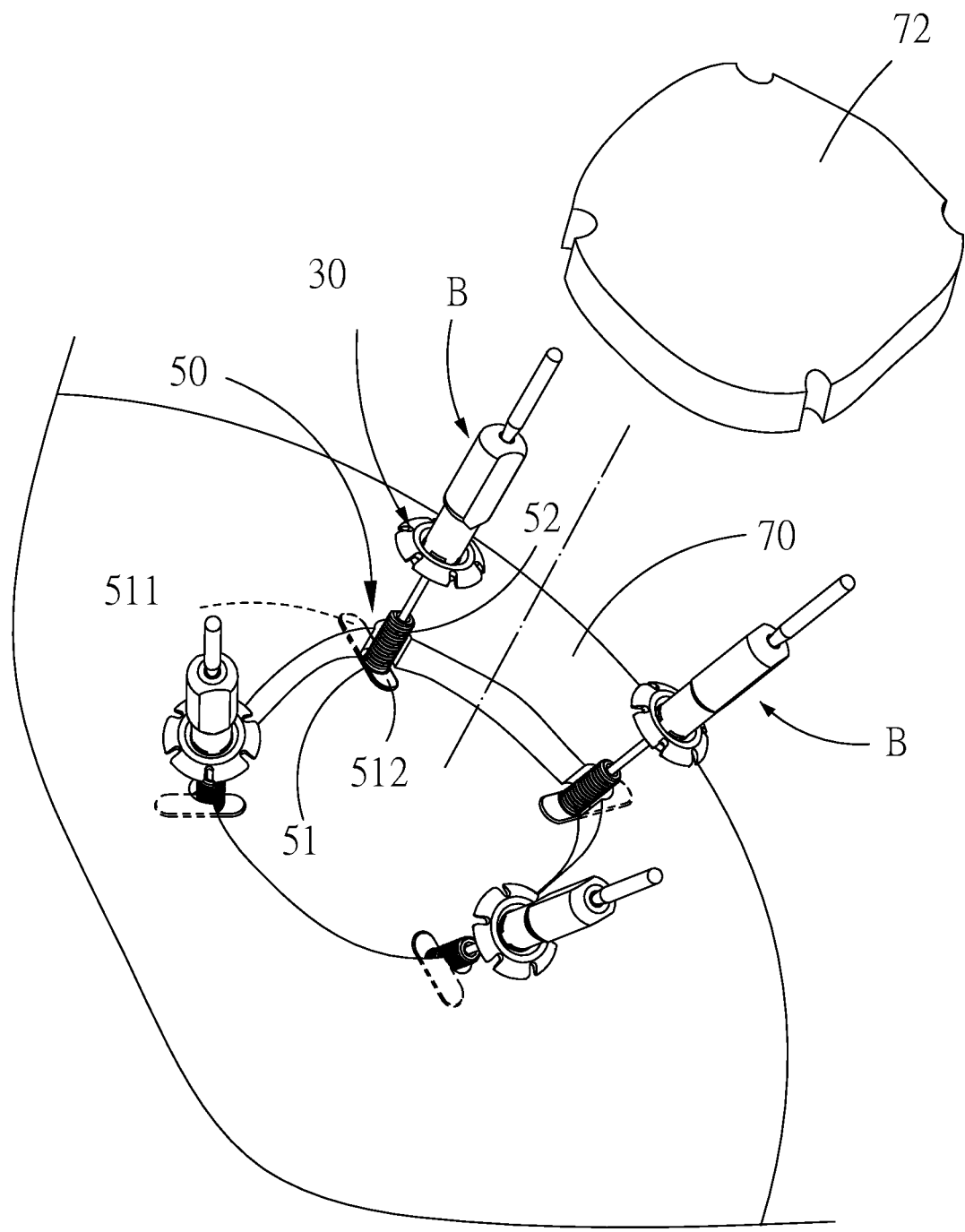
FIG. 14 is a schematic view according to an embodiment of the present invention used for retaining the cranial bone and the cranium.

As shown in FIG. 14, the present invention is used for retaining the cranial bone. The bone drilling cover device A of the present invention is first coupled with the surgical tool B to form an integral assembly, which facilitates the bone drilling cover device A and the surgical tool B to be directly placed in the drilled hole 73 of the cranium 70 simultaneously. The second base portion 51 of the lower fastening member 50 of the present invention has the first arm 511 and the second arm 512 in different lengths to span and hold the cranial bone 72 and the cranium 70. Then, the upper fastening member 30 is moved downwardly by the surgical tool B to screw the nut 33 downwardly to the second coupling portion 52 (screw rod), such that the upper fastening member 30 and the first arm 511 and the second arm 512 of the lower fastening member 50 are driven and fastened to generate a clamping force for retaining the cranial bone 72 to the cranium 70. It is convenient and quick for operation.

Figure 3:
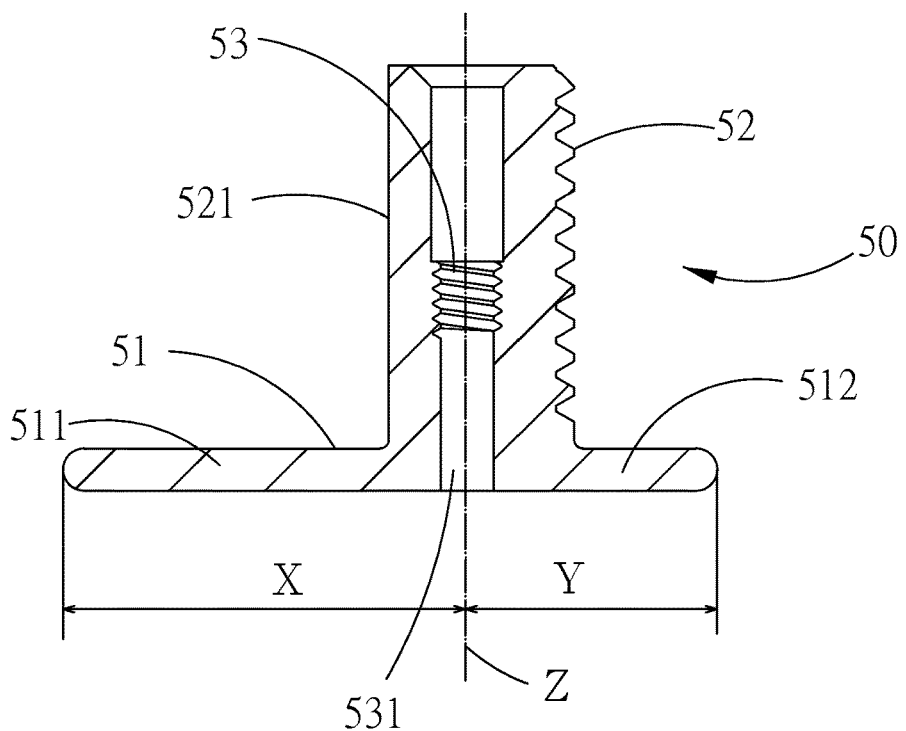
FIG. 3 is a cross-sectional view of the upper fastening member of the present invention.
Figure 4:
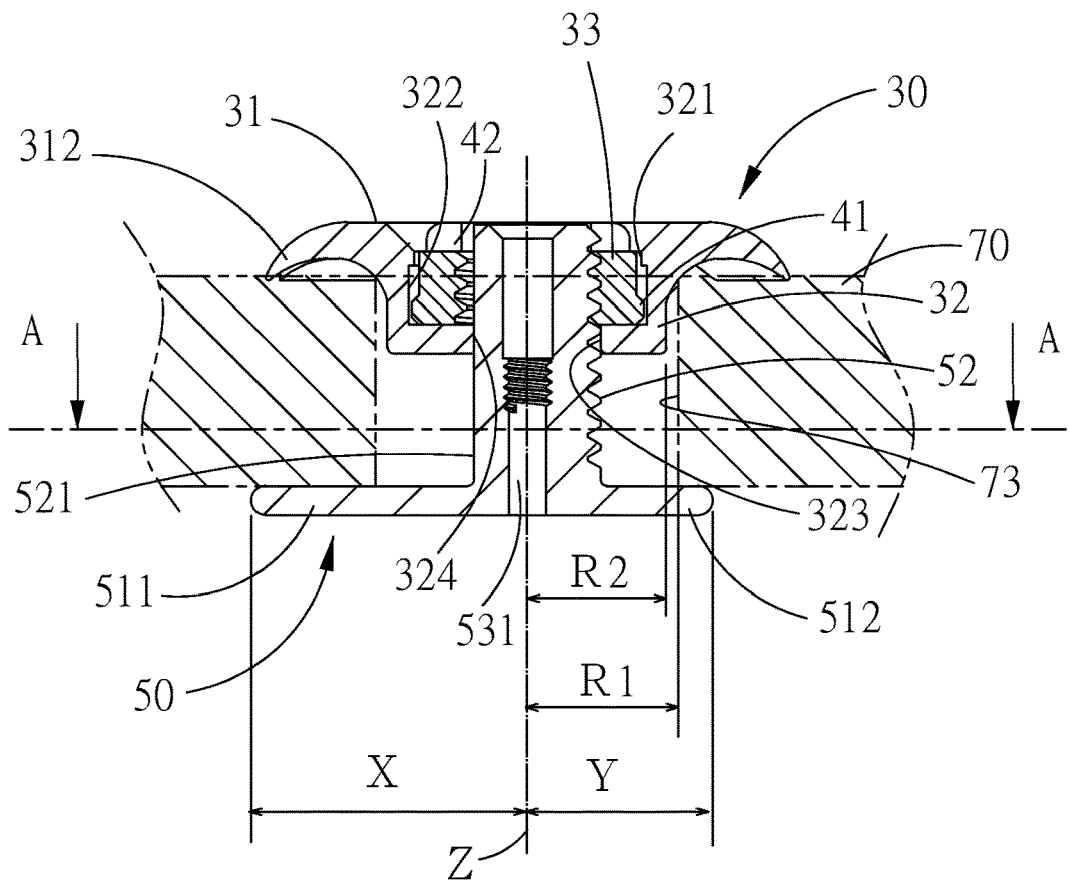
FIG. 4 is a cross-sectional view of the present invention used for covering the drilled hole of the cranial bone.
Figure 15:
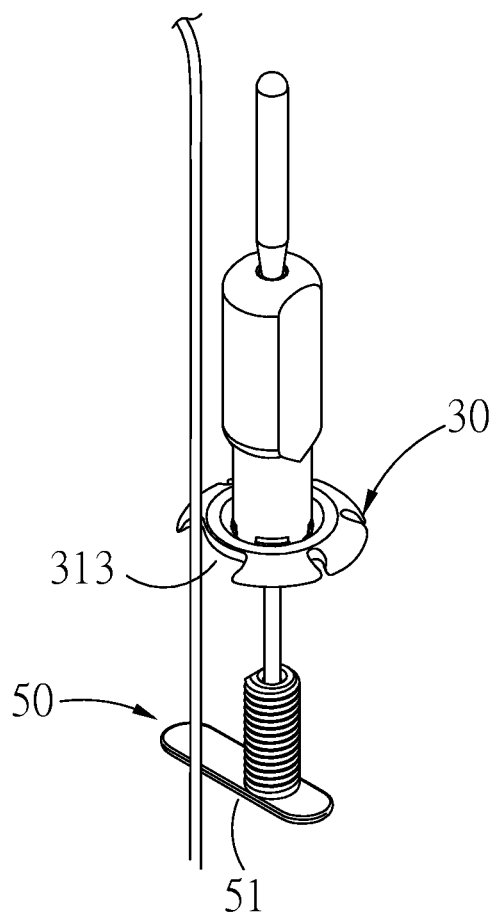
FIG. 15 is a schematic view showing that the upper fastening member is formed with a notch by cutting one of the pedal-like segments offset from the second base portion for insertion of the drainage tube according to the present invention.
Figure 16:
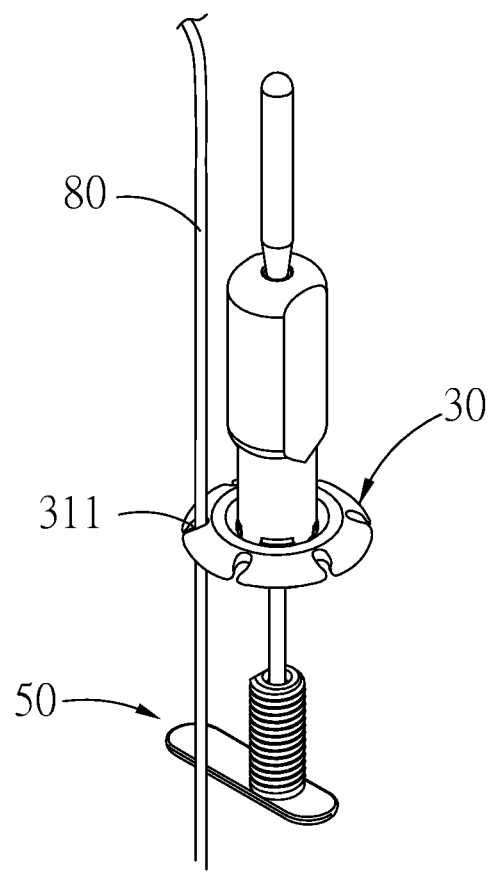
FIG. 16 is a schematic view showing that the drainage tube is inserted in one of the slits of the upper fastening member offset from the second base portion according to the present invention.

When the present invention is used for retaining the cranial bone and has the function of adding a drainage tube, as shown in FIG. 3 and FIG. 4, the inner screw hole 53 of the second coupling portion 52 (screw rod) extends downwardly and passes through the second base portion 51 to form a perforation 531 for insertion of a drainage tube (not shown); or as shown in FIG. 15, one of the pedal-like segments 312 of the first base portion 31 of the upper fastening member 30, at a position offset from the lower fastening member 50, is cut to form a notch 313 for insertion of the drainage tube; or as shown in FIG. 16, each of the slits 311 of the upper fastening member 30 is shaped like a keyhole, having an opening 314 less than the diameter of the drainage tube 80 and a limiting hole 315 greater than the diameter of the drainage tube 80 to allow the drainage tube 80 to be received and positioned therein. Since the second base portion 51 of the lower fastening member 50 of the invention is in a platy shape having a proper width, no matter what kind of structure shown in FIG. 15 and FIG. 16, there is no need to make any structural change. The cover device can be widely used.

The above-mentioned bone drilling cover device A of the present invention is applied to cover a drilled hole 73 of any bone. After the cranial bone 72 is retained, same as the prior art, the outer sleeve 60 of the surgical tool B is moved upwardly through a reverse rotation so that the surgical tool B is quickly removed from the bone drilling cover device A. Conversely, if the bone drilling cover device A or the cranial bone 72 is to be removed, the device 10 can be removed from the cranium (skull) 70 as long as the reverse operation is performed. The present invention is easy and convenient in operation for both implantation and removal.

Compared with the prior art, the bone drilling cover device A of the present invention provides the following advantages:

1. The first arm 511 and the second arm 512 of the lower fastening member 50 of the invention have different lengths, and the width is less than the diameter of the drilled hole 73. The lower fastening member 50 is inserted in an oblique manner toward the drilled hole 73, such that the first arm 511 and the second arm 512 can be inserted in an oblique manner and positioned to the underside of the drilled hole 73 for covering the drilled hole 73 of any bone. The operation is very quick and easy. The diameter of the drilled hole 73 is minimized for reducing damage to the bone structure.

2. The invention is aimed at retaining the cranial bone. The first arm 511 and the second arm 512 in different lengths are configured to span and hold the cranial bone 72 and the cranium 70 for bone drilling or retaining the cranial bone to the drilled hole of the any bone. The device can be widely used.

3. When the present invention is used for retaining the cranial bone, it is necessary to add the drainage tube 80. Since the second base portion 51 is in a platy shape having a proper width and is composed of the first and second arms in different lengths, there is no need to make any structural change, and only the upper fastening member 30 is modified. There is no need to modify the lower fastening member 50, which saves the manufacturing cost effectively.

4. In addition to the above-mentioned excellent effects and improvements, the effects of the prior art are also kept, and the functional benefits of the present invention are more enhanced and improved.

Figure 17:
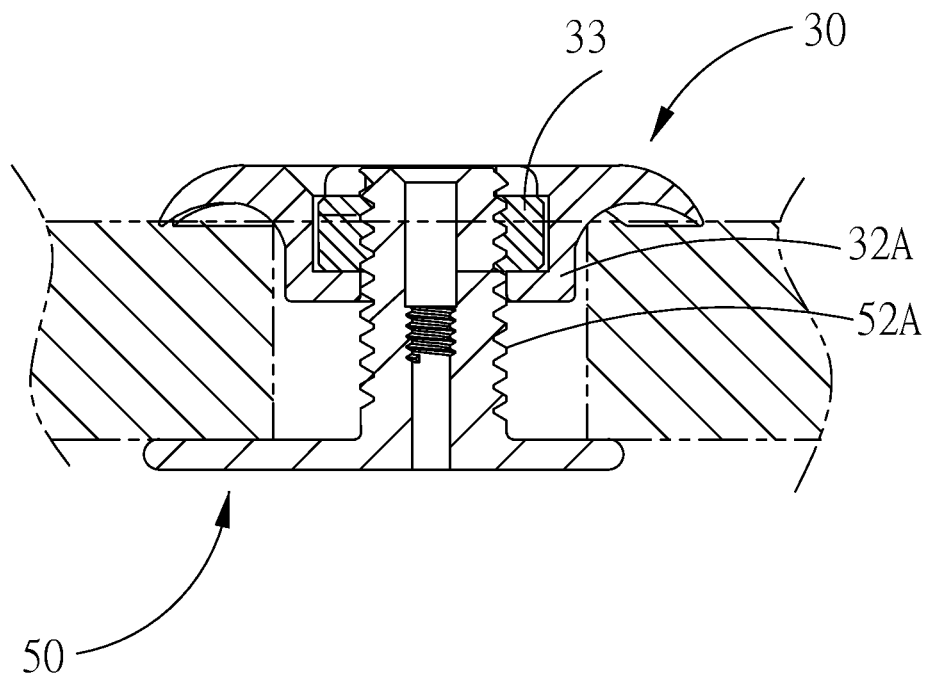
FIG. 17 is a schematic view showing that the first coupling portion is in the form of an annular sleeve and a nut and the second coupling portion is in the form of a screw rod according to another embodiment of the present invention.
Figure 18:
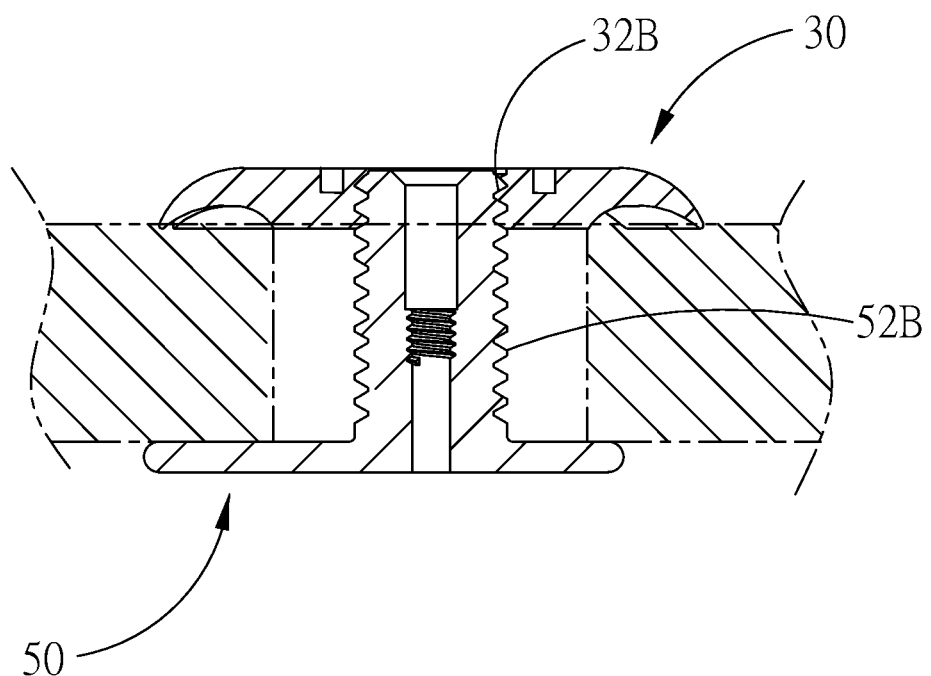
FIG. 18 is a schematic view showing that the first coupling portion is in the form of a screw hole and the second coupling portion is in the form of a screw rod according to the present invention.
Figure 19:
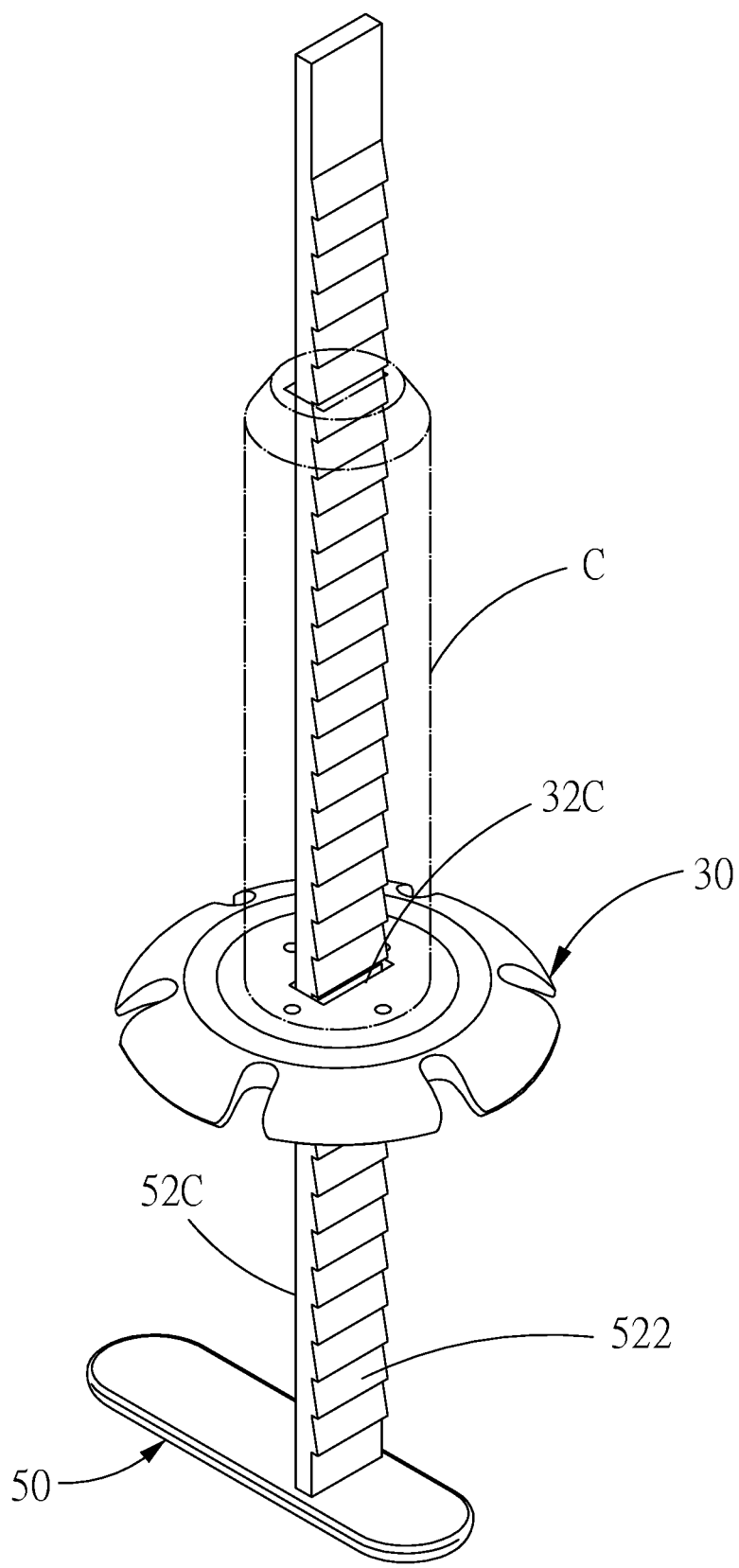
FIG. 19 is a schematic view showing that the first coupling portion is in the form of an engaging hole and the second coupling portion is in the form of a fastening strip according to the present invention.
Figure 20:
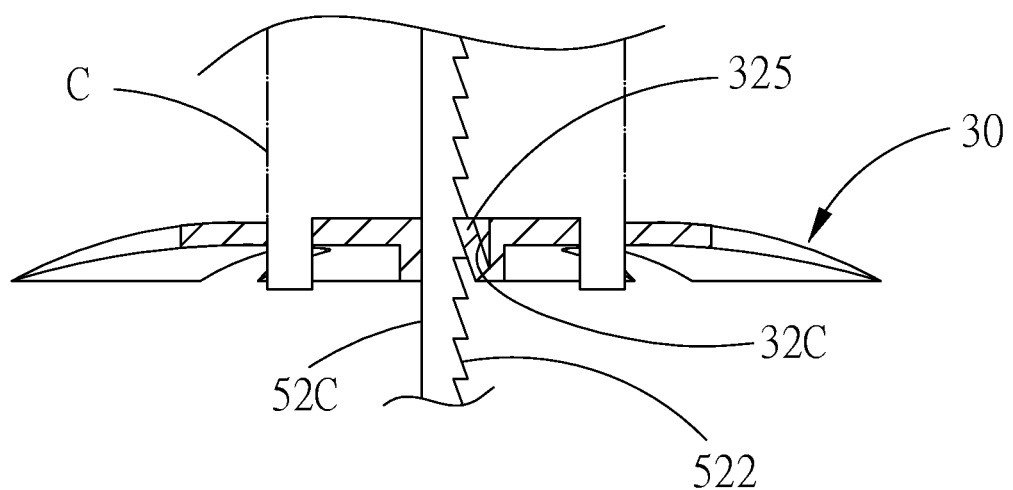
FIG. 20 is a partial sectional view of FIG. 18.
Figure 21:
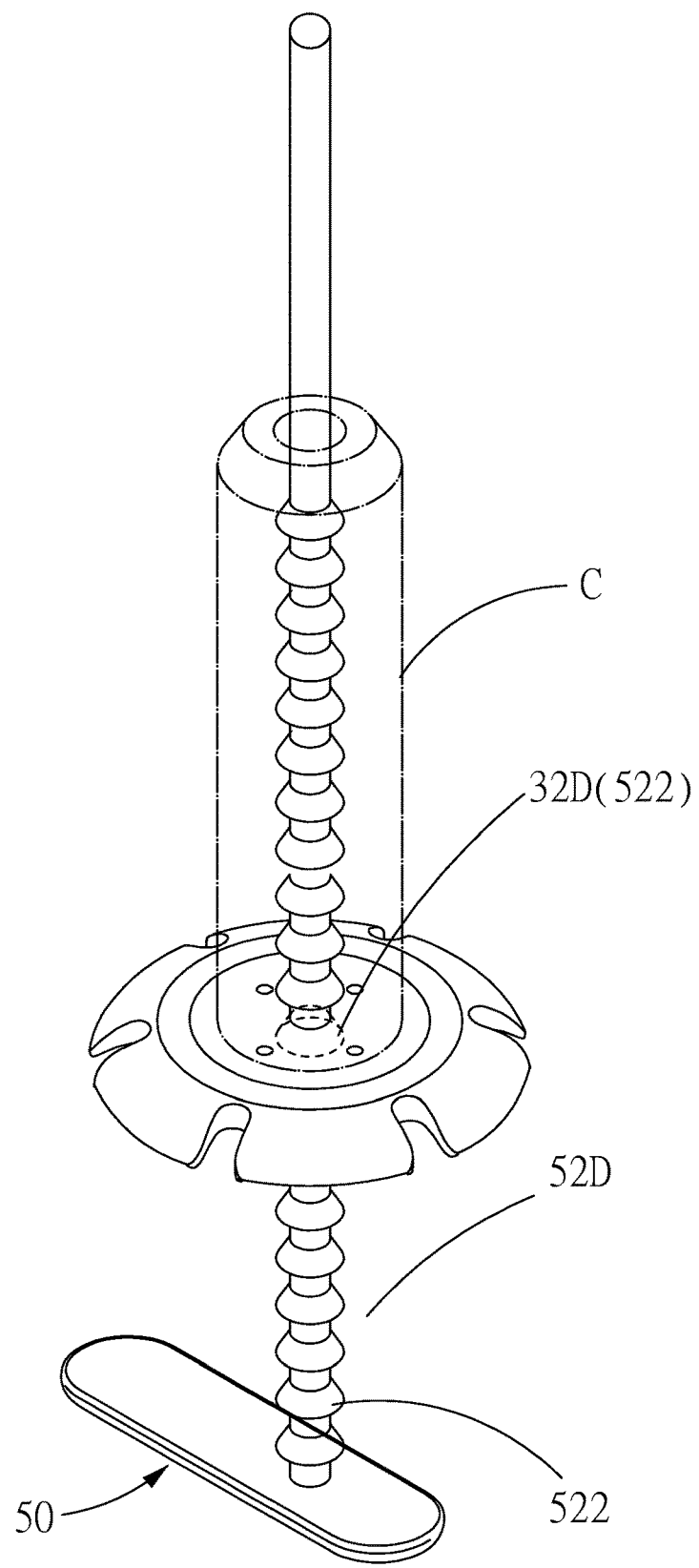
FIG. 21 is a schematic view showing that the first coupling portion is in the form of a conical engaging hole and the second coupling portion is in the form of a rod-shaped strip according to the present invention.

Furthermore, the first coupling portion 32 and the second coupling portion 52 of the present invention may be coupled to each other in different ways. In addition to the above-described coupling way, as shown in FIG. 17, the first coupling portion 32A is in form of an annular sleeve and a nut that are simply fitted, and the second coupling portion 52A is in the form of a screw rod; or as shown in FIG. 18, the first coupling portion 32B and the second coupling portion 52B are respectively formed with an inner screw hole and a screw rod to be coupled to each other; or as shown in FIG. 19 and FIG. 20 illustrating a first example of a fastening strip, the first coupling portion 32C is in the form of an engaging hole having a resilient catching portion 325 therein, the second coupling portion 52C is in the form of a long strip having a proper length, and at least one side of the strip is provided with a toothed engaging portion 522 that is engagable with the catching portion 325; or as shown in FIG. 21 illustrating a second example of a fastening strip, the first coupling portion 32D is in the form a conical engaging hole that is tapered upwardly, and the second coupling portion 52D is in the form of an elongated rod-shaped strip, and the rod-shaped strip is provided with a plurality of spaced conical engaging portions 522 that are engagable with the conical engaging hole. After the strip is inserted into the engaging hole, the upper fastening member 30 is driven by the surgical tool C to be moved toward the lower fastening member 50 for retaining the bone drilling cover device A.

In summary, the device of the invention may be used for covering the drilled hole of any bone and for retaining the cranial bone. The operation is easy and quick. The device can be widely used. Although particular embodiments of the present invention have been described in detail for purposes of illustration, various modifications and enhancements may be made without departing from the spirit and scope of the present invention. Accordingly, the present invention is not to be limited except as by the appended claims.

What is claimed is:

1. A bone drilling cover device, comprising an upper fastening member and a lower fastening member, the upper fastening member including a first base portion and a first coupling portion disposed on the first base portion; the lower fastening member including a second base portion and a second coupling portion that is disposed on the second base portion and engagable with the first coupling portion; the second base portion being composed of at least one first arm and at least one second arm, the first arm having a length greater than a length of the second arm, a total length of the first arm and the second arm being greater than a diameter of a drilled hole, wherein the first arm and the second arm are in a platy shape having a width less than the diameter of the drilled hole with a center line of the second coupling portion as a center, the first arm and the second arm are separate elements that are extendable and retractable and pivotally connected to each other.

2. The bone drilling cover device as claimed in claim 1, wherein the first coupling portion and the second coupling portion are a screw hole and a screw rod, respectively.

3. The bone drilling cover device as claimed in claim 2, wherein the first base portion has a first positioning portion that is disposed concavely or convexly for connecting a surgical tool.

4. The bone drilling cover device as claimed in claim 1, wherein the first coupling portion is an annular sleeve with a cavity portion having a bottom in which a through hole is formed, a nut is disposed in the cavity portion, and the second coupling portion is a screw rod to be screwed to the nut.

5. The bone drilling cover device as claimed in claim 4, wherein an inner surface of the cavity portion is recessed to form an engaging groove, an outer surface of the nut is provided with a raised ring engagable with the engaging groove, when the nut is screwed to the screw rod, the upper fastening member is not rotated synchronously, but can be moved up and down by the nut, and the nut and the upper fastening member collectively form a movable retaining assembly.

6. The bone drilling cover device as claimed in claim 5, wherein the length of the second arm is greater than a radius of the annular sleeve.

7. The bone drilling cover device as claimed in claim 5, wherein an upper end of the nut has a first positioning portion for connecting a surgical tool, and the screw rod is formed with an inner screw hole for connecting the surgical tool.

8. The bone drilling cover device as claimed in claim 7, wherein the first positioning portion is a concave-convex configuration annularly formed on a periphery of the upper end of the nut or includes at least two pits on a lower end surface of the nut, and the inner screw hole of the screw rod extends downwardly and passes through the second base portion to form a perforation for insertion of a drainage tube.

9. The bone drilling cover device as claimed in claim 4, wherein the length of the second arm is greater than a radius of the annular sleeve.

10. The bone drilling cover device as claimed in claim 4, wherein an upper end of the nut has a first positioning portion for connecting a surgical tool, and the screw rod is formed with an inner screw hole for connecting the surgical tool.

11. The bone drilling cover device as claimed in claim 10, wherein the first positioning portion is a concave-convex configuration annularly formed on a periphery of the upper end of the nut or includes at least two pits on a lower end surface of the nut, and the inner screw hole of the screw rod extends downwardly and passes through the second base portion to form a perforation for insertion of a drainage tube.

12. The bone drilling cover device as claimed in claim 1, wherein the first coupling portion is an engaging hole, the second coupling portion is a long strip having an engaging portion to engage with the engaging hole.

13. The bone drilling cover device as claimed in claim 1, wherein the length of the second arm is greater than a radius of the drilled hole.

14. The bone drilling cover device as claimed in claim 1, wherein the first arm and the second arm are in a platy shape having a width less than the diameter of the drilled hole with a center line of the second coupling portion as a center, and the first arm is integrally formed with the second arm.

15. The bone drilling cover device as claimed in claim 1, wherein the first arm is formed by extending the second coupling portion, the first arm is formed with a recess for the second arm to be received into the recess, and the second arm has a sleeve portion fitted onto the second coupling portion and is pivotable about the second coupling portion.

\* \* \* \* \*